United States Patent
Wilson, Jr.

(10) Patent No.: US 11,108,995 B2
(45) Date of Patent: Aug. 31, 2021

(54) SYSTEM AND METHOD FOR GAS DETECTION

(71) Applicant: Draeger Medical Systems, Inc., Andover, MA (US)

(72) Inventor: Richard Alexander Wilson, Jr., Friendswood, TX (US)

(73) Assignee: DRAEGER MEDICAL SYSTEMS, INC., Andover, MA (US)

(*) Notice: Subject to any disclaimer, the term of this patent is extended or adjusted under 35 U.S.C. 154(b) by 0 days.

(21) Appl. No.: 16/565,845

(22) Filed: Sep. 10, 2019

(65) Prior Publication Data

US 2020/0084421 A1 Mar. 12, 2020

Related U.S. Application Data

(60) Provisional application No. 62/729,609, filed on Sep. 11, 2018.

(51) Int. Cl.
*H04N 5/272* (2006.01)
*H04N 7/18* (2006.01)
*G06K 9/00* (2006.01)
*G01N 33/00* (2006.01)

(52) U.S. Cl.
CPC ......... *H04N 7/183* (2013.01); *G01N 33/0063* (2013.01); *G06K 9/00771* (2013.01); *H04N 5/272* (2013.01); *H04N 7/188* (2013.01)

(58) Field of Classification Search
None
See application file for complete search history.

(56) References Cited

U.S. PATENT DOCUMENTS

| | | | |
|---|---|---|---|
| 7,976,386 B2* | 7/2011 | Tran | A63F 13/06 463/36 |
| 10,623,667 B2* | 4/2020 | Hogasten | H04N 19/30 |
| 10,685,458 B2* | 6/2020 | Klapp | H04N 5/3656 |
| 10,708,517 B2* | 7/2020 | Lee | H04N 5/23238 |
| 2003/0025081 A1* | 2/2003 | Edner | G01N 21/3518 250/339.09 |
| 2004/0242220 A1* | 12/2004 | Matsunaga | G08B 13/19656 455/423 |
| 2014/0093174 A1* | 4/2014 | Zhang | G06K 9/00677 382/190 |
| 2015/0029320 A1* | 1/2015 | Wieser | G08B 13/248 348/77 |

(Continued)

OTHER PUBLICATIONS

Search Report IP.com.*
Brian Keane, User Manual X-Zone 3D Release 1.2, Revision 2.0, Feb. 3, 2016, pp. 1-69.

*Primary Examiner* — Mohammad J Rahman
(74) *Attorney, Agent, or Firm* — Nolte Lackenbach Siegel

(57) ABSTRACT

A method for gas detection including monitoring a concentration of a gas measured by a gas detection device to determine whether or not the concentration of the gas exceeds a threshold, when the concentration of the gas is determined to exceed the threshold, obtaining an image from a camera, the image capturing an area in proximity to the gas detection device at a time when the concentration of the gas is determined to exceed the threshold, annotating the obtained image to overlay a value of the concentration of the gas that exceeds the threshold on the captured area in proximity to the gas detection device, and transmitting the augmented image.

28 Claims, 6 Drawing Sheets

(56) References Cited

U.S. PATENT DOCUMENTS

| | | | |
|---|---|---|---|
| 2016/0156880 A1* | 6/2016 | Teich | H04N 5/225 |
| | | | 348/82 |
| 2016/0328612 A1* | 11/2016 | Ahn | G01N 33/0036 |
| 2016/0349228 A1* | 12/2016 | Kester | G01J 5/0896 |
| 2017/0097274 A1* | 4/2017 | Thorpe | G01M 3/38 |
| 2017/0221332 A1* | 8/2017 | Oertel | G08B 17/103 |
| 2018/0024262 A1* | 1/2018 | Madof | E21B 49/00 |
| | | | 175/50 |
| 2018/0173964 A1* | 6/2018 | Sha | H04N 5/232 |
| 2018/0206083 A1* | 7/2018 | Kumar | H04L 67/30 |
| 2018/0266944 A1* | 9/2018 | Waxman | G01J 3/44 |
| 2018/0276469 A1* | 9/2018 | Richards | G06T 7/33 |
| 2018/0321141 A1* | 11/2018 | Tsuchiya | G01M 3/38 |
| 2019/0003919 A1* | 1/2019 | Asano | G06T 7/0004 |
| 2019/0003984 A1* | 1/2019 | Kester | G01J 3/2823 |
| 2019/0114893 A1* | 4/2019 | Oertel | G08B 17/103 |
| 2019/0302013 A1* | 10/2019 | Wang | G01N 21/314 |
| 2019/0339158 A1* | 11/2019 | Yanai | G01M 3/38 |
| 2020/0232914 A1* | 7/2020 | Hirata | G06T 5/50 |

* cited by examiner

SYSTEM AND METHOD FOR GAS DETECTION

BACKGROUND OF THE INVENTION

1. Field of the Invention

The subject matter described herein generally relates to a system and method for gas detection, and in particular, the subject matter described herein generally relates to a system and a method for gas detection including an ability to obtain an image from a camera in order to overlay gas information obtained from a gas detection device onto an image of the actual area being monitored.

2. Description of the Related Art

Gas detection devices capable of measuring combustible gases and vapors are commonly deployed to industrial worksites for use in oil & gas, chemical, and emergency hazmat applications. For example, gas detection devices may be deployed during worksite turnaround during which the worksite is taken offline for planned maintenance or other activity in order to monitor the levels of combustible gases and vapors that may occur around the worksite during the turnaround. Similarly, gas detection devices may be deployed to assist on-site workers during a hole-watch activity in which the on-site workers are performing an activity in a confined space.

Conventionally, when it is determined that a gas detection device enters an alarm state and the reason for the alarm is not readily apparent, it is necessary to dispatch a response team to the location of the gas detection device to determine the cause of the alarm. As a result of the dispatching the response team, it becomes necessary to postpone or shut down worksite operations while the investigation is underway, thereby negatively affecting operations and possibly incurring costs and production losses.

In many instances, the alarm state of the gas detection device may be triggered by known environmental or working conditions that do not constitute a danger but nonetheless are a triggering event that would cause the alarm state of the gas detection device to be triggered. For example, an alarm state of a gas detection device could be caused by an EM (electromagnetic) field induced error in the internal electronics of the gas detection device, or a monitoring system for carbon-monoxide gas near a liquefied carbon-monoxide gas storage tank farm might also be triggered by the exhaust fumes of a delivery vehicle, forklift, etc. momentarily passing or parking nearby.

Accordingly, there exists a problem that in many instances an alarm state of a gas detection device is a false alarm state that does not constitute a danger but still must by investigated resulting in worksite operational delays.

Although cameras are strategically placed in an industrial worksite to provide worksite security and to watch over work crews, particularly in areas where direct supervision is limited or obscured by the physical properties of the worksite, coordination of data received from gas detection devices also deployed to the worksite and images obtained from cameras deployed to the worksite has not been conventionally implemented, that is, the gas detection devices and the cameras are deployed as separate packages to the worksite.

Accordingly, in order to use the deployed cameras to investigate the cause of an alarm state of the deployed gas detection device, it would be necessary to manually obtain archived images obtained from the cameras and combine the obtained images with data obtained from the gas detection device. Such actions can be time-consuming and contribute to worksite operational delays during an investigation of the cause of an alarm state of the gas detection device.

In view of the above, there exists a need in the art to reduce worksite operational delays by quickly and efficiently determining whether an alarm state of a gas detection device is a true alarm state constituting a danger.

BRIEF SUMMARY OF THE INVENTION

Accordingly to an aspect of the present invention, a method for gas detection performed using a gas detection device and a camera capable of capturing an image of an area in proximity to the gas detection device comprises: monitoring a concentration of a gas measured by the gas detection device to determine whether or not the concentration of the gas exceeds a threshold; when the concentration of the gas is determined to exceed the threshold, obtaining the image from the camera, the image capturing the area in proximity to the gas detection device at a time when the concentration of the gas is determined to exceed the threshold; augmenting the obtained image to overlay a value of the concentration of the gas that exceeds the threshold on the captured area in proximity to the gas detection device; and transmitting the augmented image.

According to another aspect of the present invention, a system for gas detection comprises: a gas detection device capable of measuring a concentration of a gas and wirelessly transmitting the concentration of the gas; a camera capable of capturing an image of an area in proximity to the gas detection device and wirelessly transmitting the image; and a computer that is wirelessly connected to the gas detection device to receive the concentration of the gas, and wirelessly connected to the camera to receive the image of the area in proximity to the gas detection device, wherein the computer determines whether or not the concentration of the gas received from the gas detection device exceeds a threshold, and wherein when the concentration of the gas is determined to exceed the threshold, the computer (i) obtains the image from the camera, the image capturing the area in proximity to the gas detection device at a time when the concentration of the gas is determined to exceed the threshold, (ii) augments the obtained image to overlay a value of the concentration of the gas that exceeds the threshold on the captured area in proximity to the gas detection device, and (iii) transmit the augmented image.

According another aspect of the present invention, a method for gas monitoring comprises: displaying a map image of a worksite, the map image including (i) a first icon representing a gas detection device capable of measuring a concentration of a gas and (ii) a second icon representing a camera capable of capturing an image of an area in proximity to the gas detection device; obtaining the image from the camera; augmenting the obtained image to overlay a value of the concentration of the gas at the time when the image was obtained from the camera on the captured area in proximity to the gas detection device; and displaying the augmented image so as to be overlaid on the displayed map image; monitoring the concentration of the gas measured by the gas detection device to determine whether or not the concentration of the gas exceeds a threshold; and when the concentration of the gas is determined to exceed the threshold, altering a characteristic of the displayed augmented image to indicate that the concentration of the gas is determined to exceed the threshold.

According another aspect of the present invention, a system for gas monitoring comprises: a gas detection device capable of measuring a concentration of a gas and wirelessly transmitting the concentration of the gas; a camera capable of capturing an image of an area in proximity to the gas detection device and wirelessly transmitting the image; and a computer that is wirelessly connected to the gas detection device to receive the concentration of the gas, and wirelessly connected to the camera to obtain the image of the area in proximity to the gas detection device, wherein the computer displays, on a display, a map image of a worksite, the map image including (i) a first icon representing the gas detection device and (ii) a second icon representing the camera, wherein the computer augments the obtained image to overlay a value of the concentration of the gas at the time when the image was obtained from the camera on the captured area in proximity to the gas detection device, wherein the computer displays, on the display, the augmented image so as to be overlaid on the displayed map image, wherein the computer determines whether or not the concentration of the gas received from the gas detection device exceeds a threshold, and wherein when the concentration of the gas is determined to exceed the threshold, the computer alters a characteristic of the displayed augmented image to indicate that the concentration of the gas is determined to exceed the threshold.

DETAILED DESCRIPTION OF THE INVENTION

Figure 1:
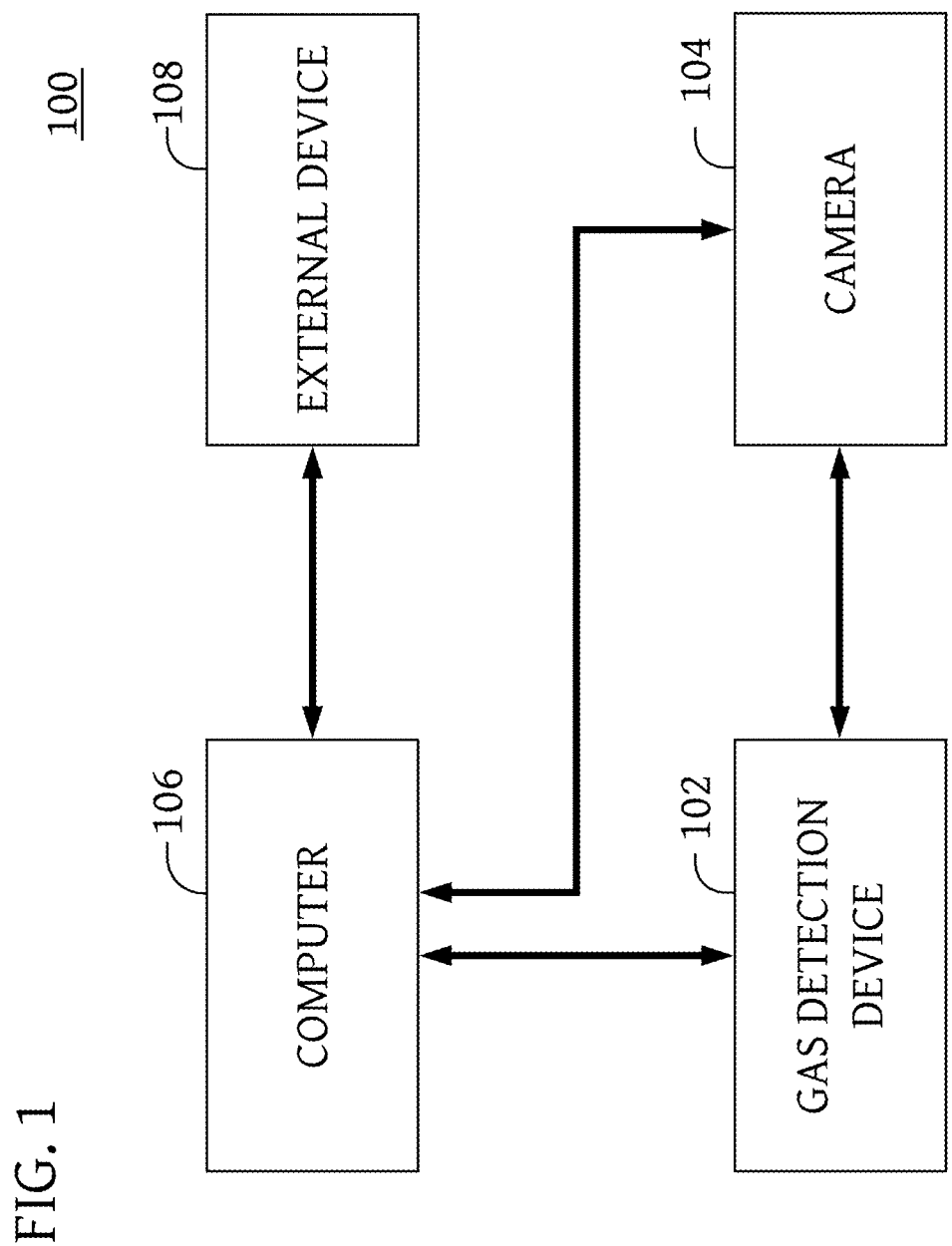
FIG. 1 illustrates a block diagram of an exemplary implementation of a gas detection system in accordance with an embodiment of the invention.

The following description is made with reference to the accompanying drawings and is provided to assist in a comprehensive understanding of various example embodiments of the present disclosure. It includes various details to assist in that understanding, but these are to be regarded as merely examples. Accordingly, those of ordinary skill in the art will recognize that various changes and modifications of the examples described herein can be made without departing from the spirit and scope of the present disclosure. In addition, descriptions of well-known functions and constructions may be omitted for clarity and conciseness.

The terms and words used in the following description and claims are not limited to the bibliographical meanings, but are merely used to enable a clear and consistent understanding of the present disclosure. Accordingly, it should be apparent to those skilled in the art that the following description of the present disclosure is provided for illustration purpose only, and not for the purpose of limiting the present disclosure as defined by the appended claims and their equivalents.

It is to be understood that the singular forms "a", "an", and "the", include plural referents unless the context clearly dictates otherwise. Thus, for example, reference to "a processor" or "a memory" includes reference to one or more of such processors or memories.

The expressions such as "include" and "may include" which may be used in the present disclosure denote the presence of the disclosed functions, operations, and constituent elements, and do not limit the presence of one or more additional functions, operations, and constituent elements. In the present disclosure, terms such as "include" and/or "have", may be construed to denote a certain characteristic, number, operation, constituent element, component or a combination thereof, but should not be construed to exclude the existence of or a possibility of the addition of one or more other characteristics, numbers, operations, constituent elements, components or combinations thereof.

In the present disclosure, the expression "and/or" includes any and all combinations of the associated listed words. For example, the expression "A and/or B" may include A, may include B, or may include both A and B.

In the present disclosure, expressions including ordinal numbers, such as "first", "second", and/or the like, may modify various elements. However, such elements are not limited by the above expressions. For example, the above expressions do not limit the sequence and/or importance of the elements. The above expressions are used merely for the purpose of distinguishing an element from the other elements. For example, a first box and a second box indicate different boxes, although both are boxes. For further example, a first element could be termed a second element, and similarly, a second element could also be termed a first element without departing from the scope of the present disclosure.

Unless otherwise defined, all terms including technical and/or scientific terms used herein have the same meaning as commonly understood by one of ordinary skill in the art to which the present disclosure pertains. In addition, unless otherwise defined, all terms defined in generally used dictionaries may not be overly interpreted.

FIG. 1 illustrates an exemplary implementation of a gas detection system 100 in accordance with an embodiment of the present invention. It should be noted that the present invention is not limited to the embodiment illustrated in FIG. 1, and that one of ordinary skill in the art would find it apparent that the present invention may be differently implemented.

As illustrated in FIG. 1, the gas detection system 100 includes a gas detection device 102, a camera 104, a computer 106, and an external device 108.

The gas detection device 102 includes one or more sensors capable of measuring, for example, combustible gases and vapors as well as O2 and harmful concentrations of Amines, Cl2, CO, CO2, COCl2, H2, H2S, HCN, NH3, NO, O3, Odorants, NO2, PH3, SO2, and organic vapors. The gas detection device 102 includes a radio device for wirelessly communicating with the camera 104 and the computer 106 via a network using, for example, the Modbus RTU communication protocol to provide a communication link between the computer 106 and the radio device. Additionally, the gas detection system 100 is not limited to only the gas detection device 102 and may comprise a plurality of gas detection devices capable of performing the same functions as the gas detection device 102. Each of the plurality of gas detection devices is assigned a unique identifier for use in the network.

The camera 104 is capable of capturing high definition video or still images within a field of view of the camera 104. Preferably, the camera 104 is able to capture high definition video or still images during day or night and in any environmental condition. The camera 104 includes a radio device for wirelessly communicating with the gas detection device 102 and the computer 106 via a network using, for example, the Modbus RTU communication protocol. The camera 104 may be deployed to the worksite as part of the gas detection system 100 or may be previously deployed to the worksite for some other purpose, for example, anti-vandalism and worksite security. In the case of the camera 104 being previously deployed to the worksite, the open network video interface forum (ONVIF) camera protocol allows the camera 104 to be discovered by the computer 106 and utilized with the gas detection system 100. Additionally, the gas detection system 100 is not limited to only the camera 104 and may comprise a plurality of cameras capable of performing the same functions as the camera 104. Each of the plurality of cameras is assigned a unique identifier for use in the network.

Alternatively, the camera 104 may be integrated with the gas detection device 102, for example, the camera 104 may be incorporated into the structure of the gas detection device 102 or at the top of a pole attached to the gas detection device 102.

The computer 106 is a device capable of implementing functions of the computer 106 described below the present disclosure. The computer 106 includes a processor, a memory, an input device, an output device, and a user interface. Additionally, the computer 106 includes a radio device for wirelessly communicating with the gas detection device 102 and the camera 104 via a network using, for example, the Modbus RTU communication protocol.

The processor may be one or more central processing units (CPUs), microprocessors, and/or other hardware devices suitable for retrieval and execution of instructions stored in the memory and/or another storage device. The processor may fetch, decode, and execute program instructions (i.e., a program) to perform the functions of the computer 106, as described below. As an alternative or in addition to retrieving and executing instructions, the processor 110 may include one or more electronic circuits comprising a number of electronic components for performing the functionality of one or more of instructions.

The memory may be any non-transitory machine-readable storage medium for maintaining data accessible to the computer 106. For example, the memory may include one or more hard disk drives, solid state drives, tape drives, and/or any other storage devices. The storage devices may be located in the computer 106 and/or in another device that is in communication with the computer 106. For example, the memory may be any electronic, magnetic, optical, or other physical storage device that stores executable instructions. Thus, the memory may be, for example, Random Access Memory (RAM), an Electrically-Erasable Programmable Read-Only Memory (EEPROM), a storage drive, an optical disc, and the like.

The input device may include hardware and/or software components that are configured to allow the computer 106 to receive data and information, via wired and/or wireless communication, from other electronic devices, such as another computer, a server, a handheld device, a removable storage medium, and the like.

The output device may include a display, such as a liquid crystal display, a touch screen, a speaker, a printer, and/or hardware and/or software components that are configured to allow the computer 106 to output data and information, via wired and/or wireless communication, to other electronic devices, such as a computer, a server, a handheld device, a removable storage medium, and the like.

The user interface may include a keyboard, a mouse, a microphone, a touch screen, and the like for allowing a user to interact with the gas detection system 100.

The program instructions executed by the computer 106 to perform the functions of the computer 106 described below can be created using one or more programming languages such as, e.g., Java®, C, C++, C #, Visual Basic®, VB.NET, Perl, Ruby®, Python, or other programming languages, possibly using object oriented design and/or coding techniques.

The external device 108 is a device that is external to the network connecting the gas detection device 102, the camera 104, and the computer 106. The external device 108 communicates with the computer 106 via a messaging method set in advance such as instant message, text messaging, e-mail, or any other suitable messaging method, thereby allowing an interested party to obtain messages from the computer 106. Examples of the external device 108 includes a tablet, a cell phone or smartphone, or another computer. However, one of ordinary skill in the art would understand that the external device 108 is not limited to these examples, and the external device 108 may be any device capable of receiving a message from the computer 106.

Figure 2:
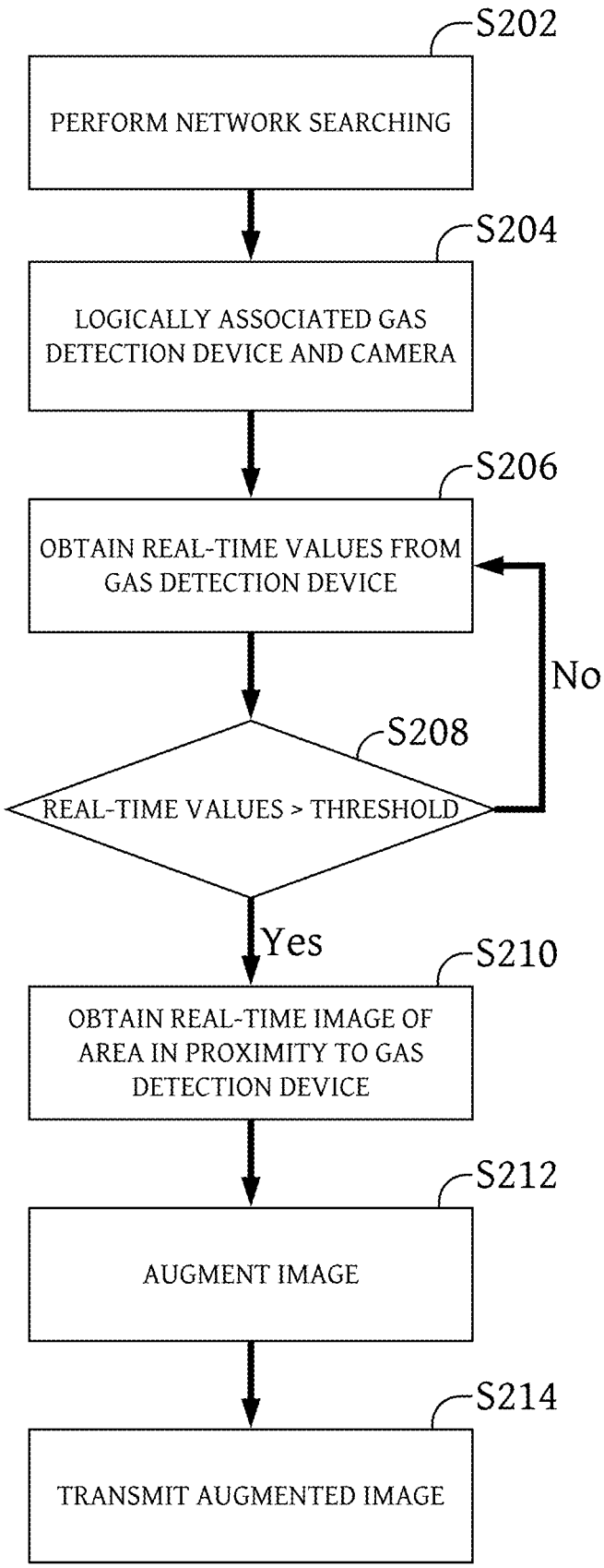
FIG. 2 illustrates a flowchart of an exemplary method performed by the gas detection system in accordance with an embodiment of the present invention.

FIG. 2 illustrates a flowchart of an exemplary method 200 performed by the gas detection system 100 in accordance with an embodiment of the present invention.

Upon initialization of the gas detection system 100, the computer 106 connects to a network and performs network device discovery for discovering devices connected to the network (S202). Upon discovery of the gas detection device 102 and the camera 104, the computer 106 connects to the gas detection device 102 and camera 104 and logically associates the gas detection device 102 and the camera 104 (S204).

Alternatively, upon connecting to the gas detection device 102 and the camera 104, the computer 106 may allow a user to perform an action to cause the gas detection device 102 to be logically associated with the camera 104. For example, the computer 106 may display a text box in which the gas detection device 102 and the camera 104 are listed, and a user is able to logically associate the gas detection device 102 and the camera 104 by selecting both a checkbox, radio button, or other indicating option next to the gas detection device 102 and a checkbox, radio button, or other indicating option next to the camera 104.

Additionally, the computer 106 is not limited to discovering only the gas detection device 102 and the camera 104, as the computer 106 may discover any number of gas detection devices and any number of cameras which may be connected via the network. In such a case, the textbox displayed by the computer 106 will list each discovered device in a separate row with a corresponding checkbox, radio button, or other indicating option thereby allowing multiple gas detection devices to be logically associated with a camera or multiple cameras to be logically associated with a gas detection device.

After connecting with the gas detection device 102, the computer 106 continuously receives values of concentrations of gases measured by the gas detection device 102 (S206). For example, the computer 106 may receive the values of concentrations of the gases measured by the gas detection device 102 at regular time intervals defined in terms of many times a second, seconds, minutes, or hours. However, the computer 106 is not limited to receiving the values of the concentrations in this manner, for example, the computer 106 may receive the values of the concentrations of the gases at irregular time intervals, when requested, and/or otherwise as necessary from the gas detection device 102. Additionally, the computer 106 may store the received values in the memory of the computer 106.

The computer 106 continuously monitors the received values of concentrations of the gases measured by the gas detection device 102 to determine if any of the received values exceed a threshold value set for the corresponding gas (S208). For example, the computer 106 may determine if any of the received values exceed a threshold value set for the corresponding gas upon receipt of the values of the of concentrations of the gases and/or at regular intervals defined in terms of many times a second, seconds, minutes, or hours. However, the computer 106 is not limited to performing the determination in this manner, for example, the computer 106 may determine if any of the received values exceed a threshold value set for the corresponding gas at irregular time intervals, when requested, and/or otherwise as necessary.

When the computer 106 determines that any of the received values of the concentrations of the gases measured by the gas detection device 102 exceeds the threshold value set for the corresponding gas, the computer 106 determines that the gas detection device 102 is in an alarm state and obtains an image 302 of an area in proximity to the gas detection device 102 from the camera 104 (S210).

Alternatively, along with the values, the computer 106 may receive information from the gas detection device 102 directly indicating that the gas detection device 102 is in the alarm state, and the computer 106 may obtain the image 302 from the camera 104 based on the information directly indicating that the gas detection device 102 is in the alarm state.

After obtaining the image 302 from the camera 104, the computer 106 augments the image 302 to include information 304 related to the alarm state of the gas detection device 102 (S212). Additionally, the computer 106 may store the received image 302 in the memory of the computer 106.

Figure 3:
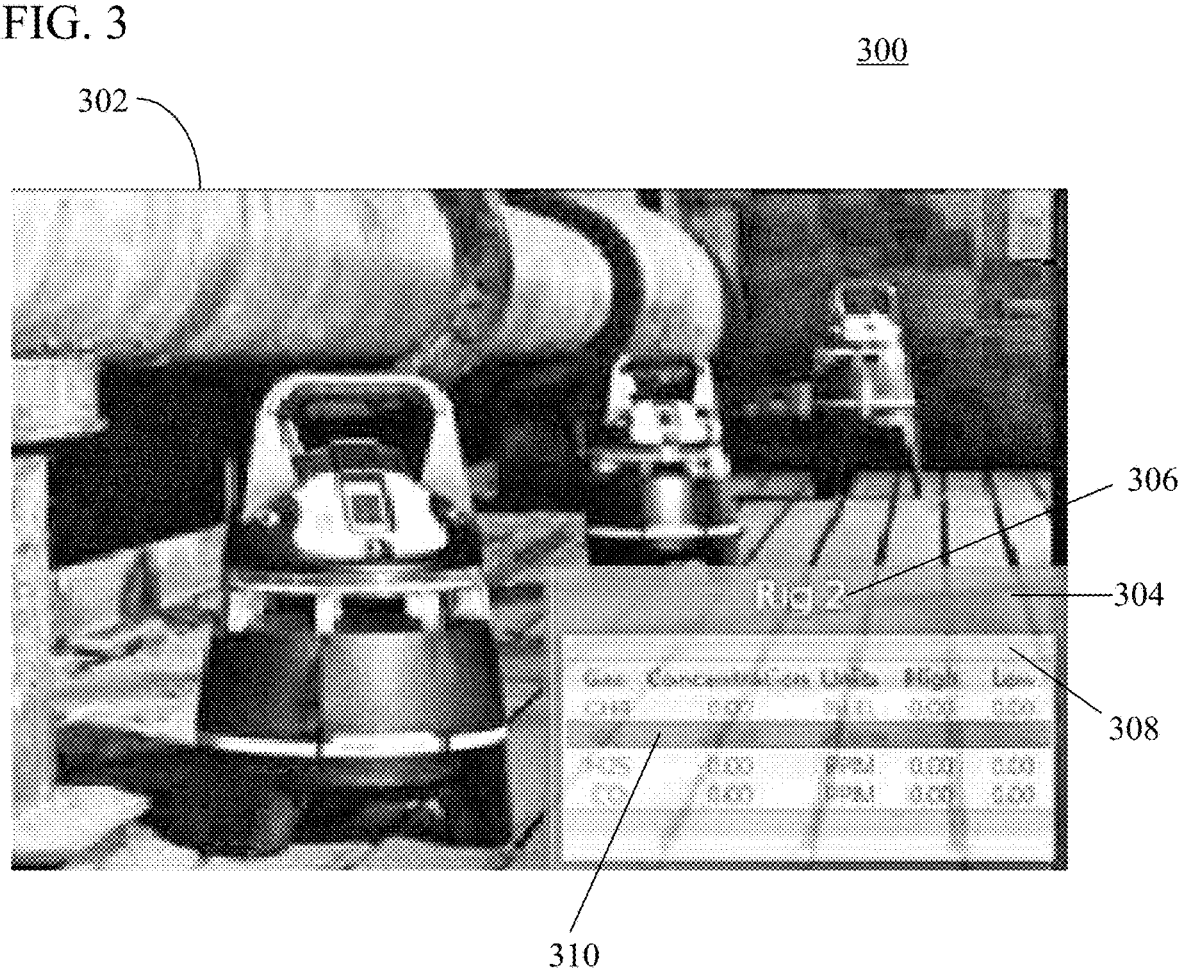
FIG. 3 is an example of the augmented image in accordance with an embodiment of the present invention.

FIG. 3 is example of the augmented image 300. As shown in FIG. 3, information 304 related to the alarm state of the gas detection device 102 is overlaid on top of the image 302 obtained from the camera 104. In the example illustrated in FIG. 3, the overlaid information 304 includes a name 306 assigned to the gas detection device 102 (here "Rig 2") and a table 308 in which different gases measured by the gas detection device 102 are associated with a measured concentration, units of measurements, high measured values, and low measured values. The name 306 may be a name that is preassigned to the gas detection device 102 or given to the gas detection device 102 by a user of the gas detection system 100 via the computer 106, and the high measured values and the low measured values may be peak values since the gas detection system 100 is initialized or since a user of the gas detection system 100 has refreshed the values via the computer 106.

Additionally, the overlaid information 304 indicates an alarming gas 310 having a measured concentration that exceeds a threshold corresponding to the alarming gas 310, where the alarming gas 310 has boldfaced text with a different color than the other displayed gases. For example, the alarming gas 310 may be displayed using red while the remaining gases may be displayed using green. The overlaid information 304 may further include identification information identifying the gas detection device 102 and the camera 104. Such identification information could include, for example, a serial number or a user designated identifier for the gas detection device 102 or the camera 104.

Further, although not illustrated, the overlaid information 304 may include further information regarding a state of the gas detection device 102, for example, the overlaid information 304 may further include a battery state of the gas detection device 102 indicating a charge of a battery powering the gas detection device 102, a remaining life of a battery powering the gas detection device 102, or an alert indicating a low charge of a battery powering the gas detection device 102.

Although the overlaid information 304 in FIG. 3 is transparent and the alarming gas 310 has boldfaced text with a different color than the other gases, one of ordinary skill in the art would recognize that the overlaid information 304 is not limited to such a configuration, for example, the overlaid information 304 could be implemented so as to be non-transparent and the alarming gas 310 could be emphasized by other means within the capabilities of one of ordinary skill in the art.

After augmenting the image 302 obtained from the camera 104, the computer 106 transmits the augmented image 300 to the external device 108 (S214). For example, the computer 106 may transmit the augmented image 300 to the external device 108 via a messaging method set in advance such as instant message, text messaging, e-mail, or any other suitable messaging method. Additionally, the computer 106 may store the augmented image 300 in the memory of the computer 106.

Alternatively, the computer 106 may obtain and augment the image 302 at a time when the gas detection device 102 is not in the alarm state. For example, the computer 106 may obtain and augment the image 302 at regular intervals or on demand when requested by a user of the gas detection system 100.

By transmitting the augmented image 300 to the external device 108, the gas detection system 100 is able to provide a snapshot on the alarm state of the gas detection device 102 to a concerned party, thereby allowing the concerned party to quickly and efficiently evaluate the alarm state of the gas detection device 102 to determine whether the alarm state of the gas detection device 102 is a true alarm state constituting a danger or whether the alarm state of the gas detection device 102 is a false alarm state caused by some other triggering event.

By allowing the concerned party to evaluate the alarm state of the gas detection device 102 via the augmented image 300 transmitted to the external device 108, the present invention provides the benefit that an investigation of the alarm state of the gas detection device 102 may be performed remotely via the augmented image 300 thereby allowing a readily apparent false alarm state of the gas detection device 102 to be identified so as to prevent the dispatching of a response team to the worksite to investigate the alarm state of the gas detection device 102. By quickly and efficiently identifying a false alarm state of the gas detection device 102 in this manner, the detection gas system 100 of the present invention obviates the need to postpone or shut down worksite operations while an on-site investigation is carried out.

Additionally, the computer 106 may perform object recognition on the image 302 obtained from the camera 104 to determine whether the alarm state of the gas detection device 102 is a true alarm state constituting a danger or a false alarm state caused by a triggering event caused by an object, for example, a vehicle emitting exhaust nearby the gas detection device 102. Similarly, facial recognition may be utilized by the computer 106 to determine if the triggering event is caused by a worker and to identify the worker.

Alternatively, the computer 106 may transmit the image 302 obtained from the camera 104 in addition to or in lieu of the augmented image 300 to the external device 108 to allow the external device 108 to perform the object recognition or the facial recognition.

By coordinating the functions of the gas detection device 102 and the camera 104 into a the gas detection system 100, the present invention described herein provides a comprehensive full package that allows the combination of gas detection device 102 and the camera 104 to provide functionality that is not possible as individual and uncoordinated devices, thereby providing an improvement to the overall functionality of the gas detection device 102 and the camera 104.

Figure 4:
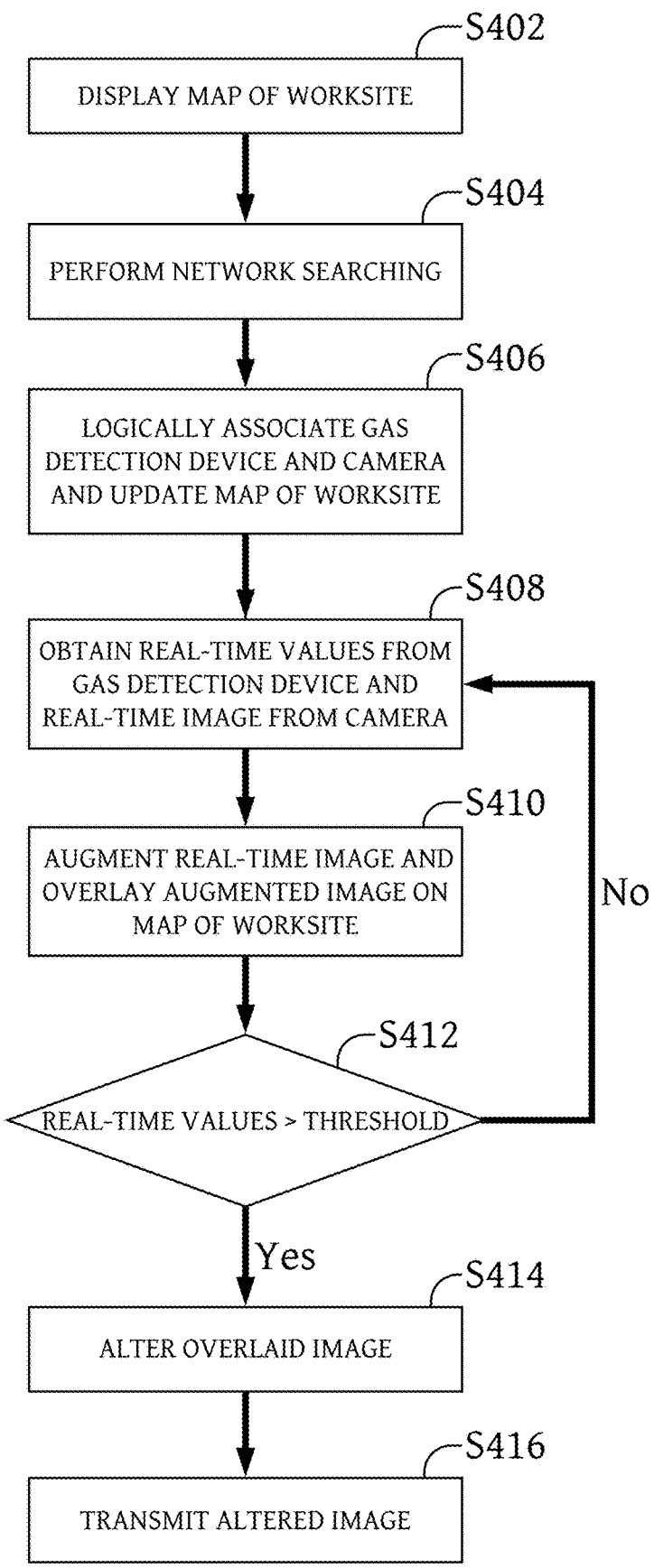
FIG. 4 illustrates a flowchart of an exemplary method 400 performed by the gas detection system in accordance with another embodiment of the present invention.

FIG. 4 illustrates a flowchart of an exemplary method 400 performed by the gas detection system 100 in accordance with another embodiment of the present invention.

Figure 5A:
FIG. 5A illustrates an example of a map of a worksite displayed by the computer upon initialization of the gas detection system.

Upon initialization of the gas detection system 100 according to this embodiment, the computer 106 displays a map of a worksite 500 (S402) and connects to a network, and the computer 106 performs network device discovery for discovering devices connected to the network (S404). FIG. 5A illustrates an example of a map of a worksite 500 displayed by the computer 106 upon initialization of the gas detection system 100 and before performing network discovery searching.

Upon discovery of the gas detection device 102 and the camera 104, the computer 106 connects to the gas detection device 102 and camera 104 and logically associates the gas detection device 102 and the camera 104 (S406).

Alternatively, upon connecting to the gas detection device 102 and the camera 104, the computer 106 may allow a user to perform an action to cause the gas detection device 102 to be logically associated with the camera 104. For example, the computer 106 may display a text box in which the gas detection device 102 and the camera 104 are listed, and a user is able to logically associate the gas detection device 102 and the camera 104 by selecting both a checkbox, radio button, or other indicating option next to the gas detection device 102 and a checkbox, radio button, or other indicating option next to the camera 104.

Additionally, the computer 106 is not limited to discovering only the gas detection device 102 and the camera 104, and the computer 106 may discover any number of gas detection devices and any number of cameras which may be connected via the network. In such a case, the textbox displayed by the computer 106 will list each discovered device in a separate row with a corresponding checkbox, radio button, or other indicating option thereby allowing multiple gas detection devices to be logically associated with a camera or multiple cameras to be logically associated with a gas detection device.

Figure 5B:
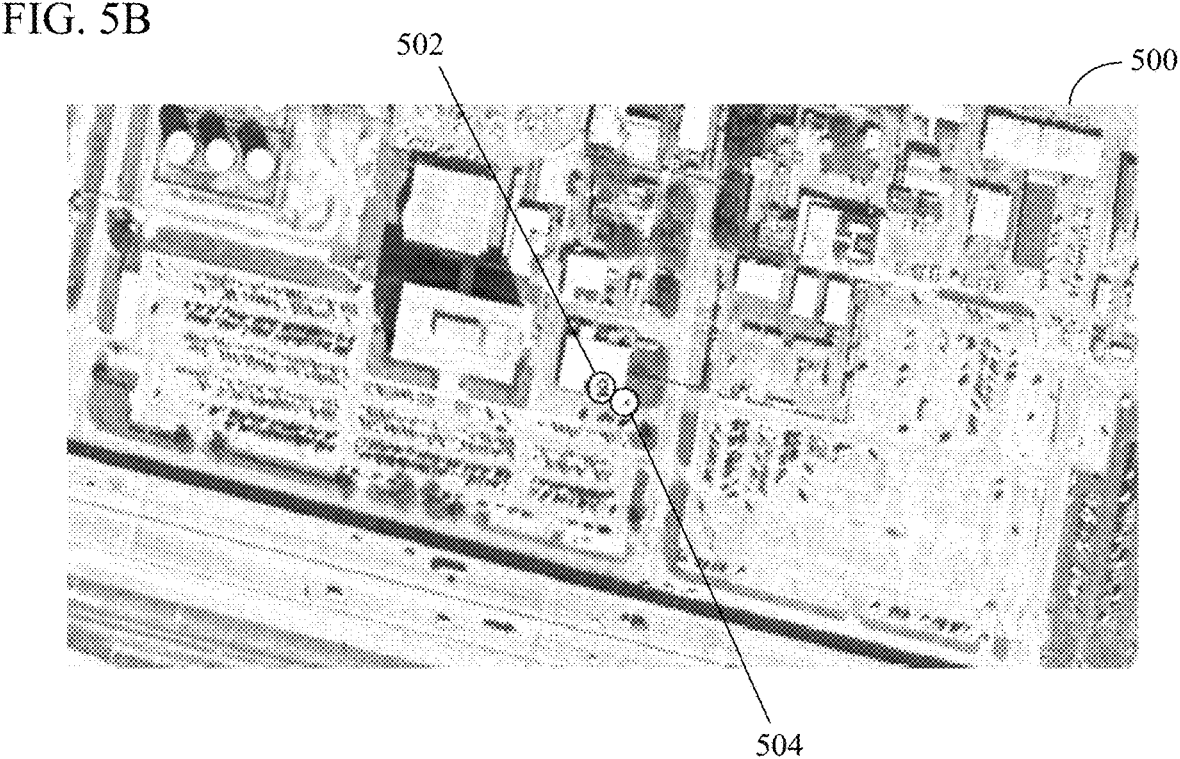
FIG. 5B illustrates an example of a map of the worksite displayed by the computer after performing network discovery searching.

After connecting with and logically associating the gas detection device 102 and the camera 104, the computer 106 updates and displays the map of the worksite 500. FIG. 5B illustrates an example of the map of the worksite 500 displayed by the computer 106 after gas detection device 102 and camera 104 have been discovered and logically associated with one another.

As can be seen in FIG. 5B, upon discovery of the gas detection device 102 and the camera 104, an icon 502 representing the gas detection device 102 and an icon 504 representing the camera 104 are displayed on the map of the worksite 500. A user may manipulate the map of the worksite 500 to arrange the icon 502 representing the gas detection device 102 and the icon 504 representing the camera 104 as necessary so that the icons are appropriately positioned on the map of the worksite 500.

After connecting with the gas detection device 102 and the camera 104, the computer 106 continuously receives values of concentrations of gases measured by the gas detection device 102 and an image 602 of an area in proximity to the gas detection device 102 from the camera 104 (S408). For example, the computer 106 may receive the values of concentrations of the gases and/or the image 602 at regular time intervals defined in terms of many times a second, seconds, minutes, or hours. However, the computer 106 is not limited to receiving the values of the concentrations and/or the image 602 in this manner, for example, the computer 106 may receive the values of the concentrations of the gases and/or the image 602 at irregular time intervals, when requested, and/or otherwise as necessary. Further, the timing of receiving the values of the concentrations of the gases is not necessarily the same as the timing of receiving the image 602. Additionally, the computer 106 may store the received values and/or the received image 602 in the memory of the computer 106.

The computer 106 augments the image 602 received from the camera 104 to include information related to the values of the concentrations of gases received from the gas detection device 102, and the computer 102 displays the augmented image 602 to be overlaid on the map of the worksite 500 (S410).

Figure 6A:
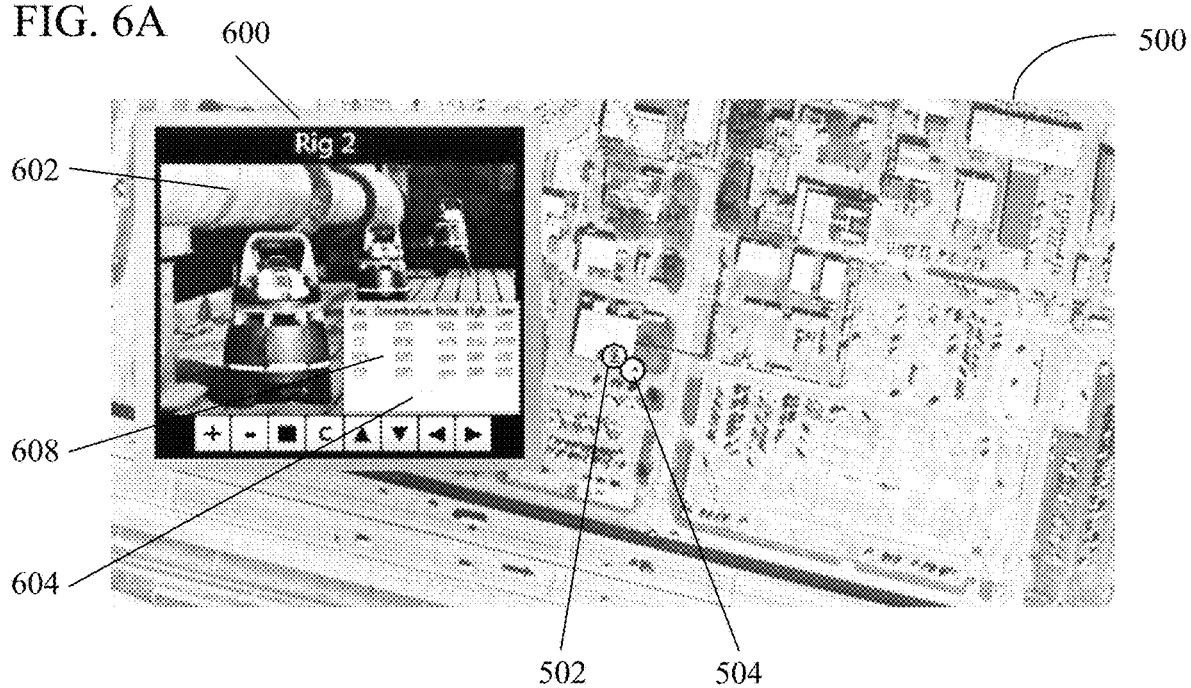
FIG. 6A illustrates an example of the map of the worksite displayed by the computer in which an augmented image is overlaid on the map of the worksite.

FIG. 6A illustrates an example of the map of the worksite 500 displayed by the computer 106 in which an augmented image 600 is overlaid on the map of the worksite 500. The augmented image 600 includes an image 602 obtained from the camera 104 which captures the area in proximity to the gas detection device 102. As shown in FIG. 6A, on top of the image 602, information 604 related to a current state of the gas detection device 102 is overlaid. In the example illustrated in FIG. 6A, the overlaid information 604 includes a name 606 given to the gas detection device 102 and a table 608 in which different gases measured by the gas detection device 102 are associated with a measured concentration, units of measurements, high measured values, and low measured values. The name 606 may be a name that is preassigned to the gas detection device 102 or given to the gas detection device 102 by a user of the gas detection system 100 via the computer 106, and the high measured values and the low measured values may be peak values since the gas detection system 100 is initialized or since a user of the gas detection system 100 has refreshed the values via the computer 106. Additionally, as shown in FIG. 6A, the icon 502 representing gas detection device 102 is highlighted in a manner to make it readily apparent that the gas detection device 102 is not in an alarm state.

The computer 106 continuously monitors the received values of concentrations of the gases measured by the gas detection device 102 to determine if any of the received values exceed a threshold value set for the corresponding gas (S412). For example, the computer 106 may determine if any of the received values exceed a threshold value set for the corresponding gas upon receipt of the values of the of concentrations of the gases and/or at regular intervals defined in terms of many times a second, seconds, minutes, or hours. However, the computer 106 is not limited to performing the determination in this manner, for example, the computer 106 may determine if any of the received values exceed a threshold value set for the corresponding gas at irregular time intervals, when requested, and/or otherwise as necessary When the computer 106 determines that any of the received values of the concentrations of the gases measured by the gas detection device 102 exceeds a threshold value set for the corresponding gas, the computer 106 determines that the gas detection device 102 is in an alarm state and alters the augmented image 600 overlaid on the map of the worksite 500 to make it apparent that the gas detection device 102 is in the alarm state (S414).

Figure 6B:
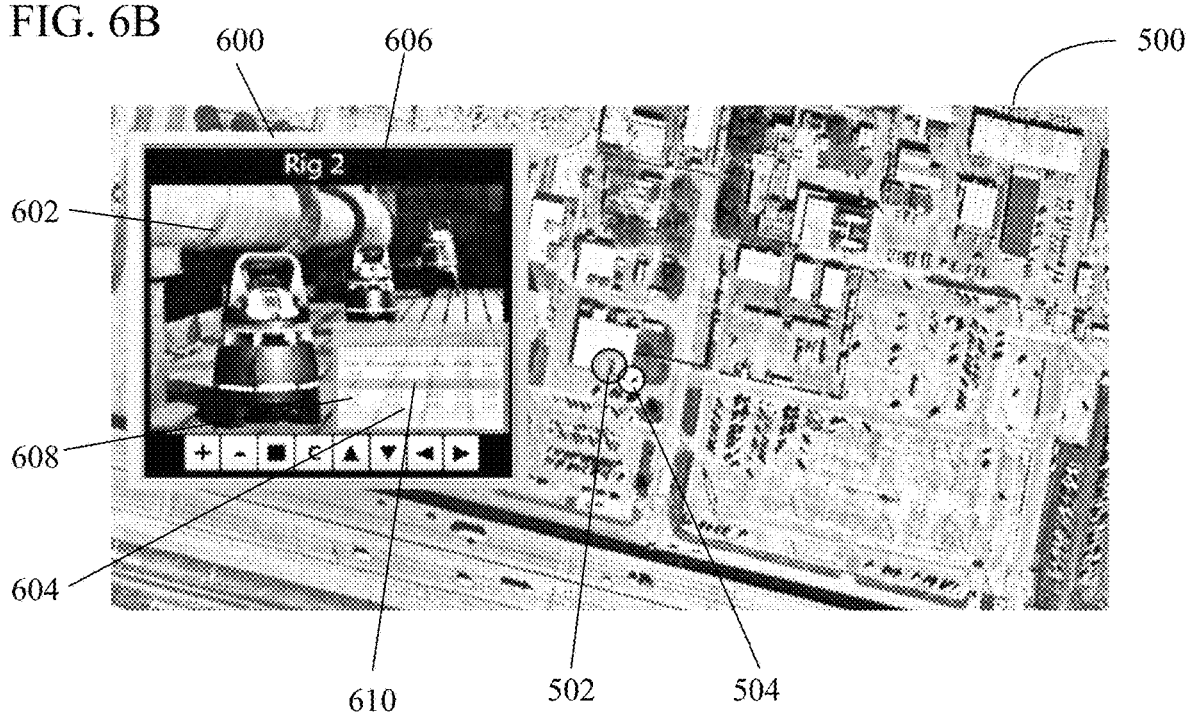
FIG. 6B illustrates an example of the map of the worksite displayed by the computer in which the augmented image is overlaid on the map of the worksite when the gas detection device is in the alarm state.

FIG. 6B illustrates an example of the map of the worksite 500 displayed by the computer 106 in which the augmented image 600 is overlaid on the map of the worksite 500 when the gas detection device 102 is in the alarm state. In contrast to FIG. 6A in which the gas detection device 102 is not in the alarm state, the overlaid information 604 in FIG. 6B is altered to indicate an alarming gas 610 having a measured concentration that exceeds a threshold corresponding to the alarming gas 610. For example, the alarming gas 610 may be displayed using red while the remaining gases may be displayed using green.

Similarly, in FIG. 6B, the icon 502 representing gas detection device 102 is altered in a manner to make it readily apparent that the gas detection device 102 is in the alarm state. For example, in FIG. 6A, the icon 502 representing gas detection device 102 may be highlighted in green to indicate that the gas detection device 102 is not in the alarm state, and in FIG. 6B, the icon 502 representing gas detection device 102 may be highlighted in red to indicate that the gas detection device 102 is in the alarm state.

The overlaid information 604 may further include identification information identifying the gas detection device 102 and the camera 104. Such identification information could include, for example, a serial number or a user designated identifier for the gas detection device 102 or the camera 104.

Additionally, although not illustrated, the overlaid information 604 may include further information regarding a state of the gas detection device 102, for example, the overlaid information 304 may further include a battery state of the gas detection device 102 indicating a charge of a battery powering the gas detection device 102, a remaining life of a battery powering the gas detection device 102, or an alert indicating a low charge of a battery powering the gas detection device 102.

Although the overlaid information 604 in FIG. 6 is transparent and the alarming gas 610 has boldfaced text with a different color than the other gases, one of ordinary skill in the art would recognize that the overlaid information 604 is not limited to such a configuration, for example, the overlaid information 604 could be implemented so as to be non-transparent and the alarming gas 610 could be emphasized by other means within the capabilities of one of ordinary skill in the art.

After the computer 106 augments the image 602 obtained from the camera 104, the computer 106 transmits the augmented image 300 to the external device 108 (S416). Additionally, the computer 106 may store the received values in the memory of the computer 106.

Alternatively, the computer 106 may obtain and augment the image 602 at a time when the gas detection device 102 is not in the alarm state. For example, the computer 106 may obtain and augment the image 602 at regular intervals or on demand when requested by a user of the gas detection system 100.

By transmitting the augmented image 600 to the external device 108, the gas detection system 100 is able to provide a snapshot on the alarm state of the gas detection device 102 to a concerned party, thereby allowing the concerned party to quickly and efficiently evaluate the alarm state of the gas detection device 102 to determine whether the alarm state of the gas detection device 102 is a true alarm state constituting a danger or whether the alarm state of the gas detection device 102 is a false alarm state caused by some other triggering event.

By allowing the concerned party to evaluate the alarm state of the gas detection device 102 via the augmented image 600 transmitted to the external device 108, the present invention provides the benefit that an investigation of the alarm state of the gas detection device 102 may be performed remotely via the augmented image 600 thereby allowing a readily apparent false alarm state of the gas detection device 102 to be identified so as to prevent the dispatching of a response team to the worksite to investigate the alarm state of the gas detection device 102. By quickly and efficiently identifying a false alarm state of the gas detection device 102 in this manner, the gas detection system 100 of the present invention obviates the need to postpone or shut down worksite operations while an on-site investigation is carried out.

Additionally, the computer 106 may perform object recognition on the image 602 obtained from the camera 104 to determine whether the alarm state of the gas detection device 102 is a true alarm state constituting a danger or a false alarm state caused by a triggering event caused by an object, for example, vehicle emitting exhaust nearby the gas detection device 102. Similarly, facial recognition may be utilized by the computer 106 to determine if the triggering event is caused by a worker and to identify the worker.

Alternatively, the computer 106 may transmit the image 602 obtained from the camera 104 in addition to or in lieu of the augmented image 300 to the external device 108 to allow the external device 108 to perform the object recognition or the facial recognition.

By coordinating the functions of the gas detection device 102 and the camera 104 into a the gas detection system 100, the present invention described herein provides a comprehensive full package that allows the combination of gas detection device 102 and the camera 104 to provide functionality that is not possible as individual and uncoordinated devices, thereby providing an improvement to the overall functionality of the gas detection device 102 and the camera 104.

While the above embodiments of the present invention have been disclosed, numerous modifications and changes will occur to those of ordinary skill in the art to which this invention pertains. The claims annexed to and forming a part of this specification are intended to cover all such embodiments and changes as fall within the true spirit and scope of the present invention.

The invention claimed is:

1. A method for gas detection performed using a gas detection device and a camera capable of capturing an image, the method comprising:
  monitoring concentrations of one or more gases measured by the gas detection device to determine whether or not the concentration of one of the monitored gases exceeds a threshold;
  when the concentration of the one of the monitored gases is determined to exceed the threshold, obtaining the image from the camera, the image capturing an area in proximity to the gas detection device at a time when the concentration of the one of the monitored gases is determined to exceed the threshold;
  augmenting the obtained image by overlaying on the image one or more numerical values of the concentration of the one of the monitored gases that exceeds the threshold on the captured area in proximity to the gas detection device, at the time when the concentration of the one of the monitored gases was determined to exceed the threshold; and
  transmitting the augmented image overlaid with the one or more numerical values of the concentration of the one of the monitored gases from the time when the concentration of the one of the monitored gases was determined to exceed the threshold.

2. The method of claim 1, wherein in the monitoring, the concentrations of the one or more gases measured by the gas detection device are continuously monitored to determine whether or not the concentration of the one of the monitored gases exceeds the threshold.

3. The method of claim 1, wherein in the transmitting, the augmented image is transmitted via a predetermined messaging technique to a predetermined party.

4. The method of claim 1, further comprising:
  performing network discovery searching of a network to discover the gas detection device and the camera, the gas detection device and the camera being connected to the network; and
  logically associating the camera with the gas detection device such that when the concentration the one of the monitored gases determined to exceed the threshold, the camera captures the image.

5. The method of claim 4, wherein the gas detection device and the camera are wirelessly connected to the network.

6. The method of claim 1, further comprising performing object recognition on the augmented image to determine whether or not the concentration of the one of the monitored gases determined to exceed the threshold is caused by a triggering event which is not a cause for an alarm.

7. The method of claim 1, wherein the camera is integrated with the gas detection device.

8. A system for gas detection, the system comprising:
  a gas detection device capable of measuring concentrations of one or more gases and wirelessly transmitting the concentrations of the one or more gases;
  a camera capable of capturing an image of an area in proximity to the gas detection device and wirelessly transmitting the image; and
  a computer that is wirelessly connected to the gas detection device to receive the concentrations of the one or more gases, and wirelessly connected to the camera to receive the image of the area in proximity to the gas detection device, wherein:
    the computer is configured to monitor the concentrations of the one or more gases received from the gas detection device to determine whether or not the concentration of one of the monitored gases exceeds a threshold, and
    when the concentration of the one of the monitored gases is determined to exceed the threshold, the computer is configured to
      (i) obtain the image from the camera, the image capturing the area in proximity to the gas detection device at a time when the concentration of one of the monitored gases is determined to exceed the threshold,
      (ii) augment the obtained image by overlaying on the image one or more numerical values of the concentration of the one of the monitored gases that exceeds the threshold on the captured area in proximity to the gas detection device, at the time when the concentration of the one of the monitored gases was determined to exceed the threshold, and
      (iii) transmit the augmented image overlaid with the one or more numerical values of the concentration of the one of the monitored gases from the time when the concentration of the one of the monitored gases was determined to exceed the threshold.

9. The system of claim 8, wherein the computer is configured to continuously monitor the concentrations of the one or more gases received from the gas detection device to determine whether or not the concentration of the one of the one of the monitored gases exceeds the threshold.

10. The system of claim 8, wherein the computer is configured to transmit the augmented image via a predetermined messaging technique to a predetermined party.

11. The system of claim 8,
  wherein to become wirelessly connected to the gas detection device and the camera, the computer is configured to perform network discovery searching of a network to discover the gas detection device and the camera, the gas detection device and the camera being connected to the network, and
  wherein after discovering the gas detection device and the camera, the computer is configured to logically associate the camera with the gas detection device such that when the computer determines that the concentration of the one of the monitored gases exceeds the threshold, the computer obtains the image from the camera.

12. The system of claim 11, wherein the gas detection device and the camera are wirelessly connected to the network.

13. The system of claim 8, wherein the computer is configured to perform object recognition on the augmented image to determine whether or not the concentration of the one of the monitored gases determined to exceed the threshold is caused by a triggering event which is not a cause for an alarm.

14. The system of claim 8, wherein the camera is integrated with the gas detection device.

15. A method for gas monitoring, the method comprising:
  displaying a map image of a worksite, the map image including (i) a first icon representing a gas detection device capable of measuring concentrations of one or more gases and (ii) a second icon representing a camera capable of capturing an image of an area in proximity to the gas detection device;
  obtaining the image from the camera;
  monitoring the concentrations of the one or more gases measured by the gas detection device to determine whether or not the concentration of one of the monitored gases exceeds a threshold;

augmenting the obtained image by overlaying on the image one or more numerical values of the concentration of the one of the monitored gases at a time when the image is obtained from the camera on the captured area in proximity to the gas detection device; and displaying the augmented image to be the least partially overlapped with the displayed map image;

when the concentration of the one or the monitored gases is determined to exceed the threshold, altering a characteristic of the displayed augmented image overlaid with the one or more numerical values of the concentration of the one of the monitored gases to indicate that the concentration of the one of the monitored gases is determined to exceed the threshold, at the time when the concentration of the one of the monitored gases was determined to exceed the threshold; and transmitting the augmented image overlaid with the one or more numerical values of the concentration of the one of the monitored gases from the time when the concentration of the one of the monitored gases was determined to exceed the threshold.

16. The method of claim 15, wherein in the monitoring, the concentrations of the one or more gases measured by the gas detection device are continuously monitored to determine whether or not the concentration of the one of the monitored gases exceeds the threshold.

17. The method of claim 15, wherein in the transmitting, the augmented image overlaid with the one or more numerical values of the concentration of the one of the monitored gases is transmitted via a predetermined messaging technique to a predetermined party.

18. The method of claim 15, further comprising:
performing network discovery searching of a network to discover the gas detection device and the camera, the gas detection device and the camera being connected to the network; and
logically associating the camera with the gas detection device such that when the concentration of the one of the monitored gases is determined to exceed the threshold, the camera captures the image.

19. The method of claim 18, wherein the gas detection device and the camera are wirelessly connected to the network.

20. The method of claim 15, further comprising performing object recognition on the augmented image to determine whether or not the concentration of the one of the monitored gases determined to exceed the threshold is caused by a triggering event which is not a cause for an alarm.

21. The method of claim 15, wherein the camera is integrated with the gas detection device.

22. A system for gas monitoring, the system comprising:
a gas detection device capable of measuring concentrations of one or more gases and wirelessly transmitting the concentrations of the one or more gases;
a camera capable of capturing an image of an area in proximity to the gas detection device and wirelessly transmitting the image; and
a computer that is wirelessly connected to the gas detection device to receive the concentrations of the one or more gases, and wirelessly connected to the camera to obtain the image of the area in proximity to the gas detection device, wherein the computer is configured to:

display, on a display, a map image of a worksite, the map image including (i) a first icon representing the gas detection device and (ii) a second icon representing the camera, monitoring the concentrations of the one or more gases received from the gas detection device to determine whether or not the concentration of one of the monitored gases exceeds a threshold, augment the obtained image by overlaying on the image one or more numerical values of the concentration of the one of the monitored gases at a time when the image is obtained from the camera on the captured area in proximity to the gas detection device, display, on the display, the augmented image to be at least partially overlapped with the displayed map image, when the concentration of the one of the monitored gases is determined to exceed the threshold, alter a characteristic of the displayed augmented image overlaid with the one or more numerical values of the concentration of the one of the monitored gases to indicate that the concentration of the one of the monitored gases is determined to exceed the threshold, at the time when the concentration of the one of the monitored gases was determined to exceed the threshold, and transmit the augmented image overlaid with the one or more numerical values of the concentration of the one of the monitored gases from the time when the concentration of the one of the monitored gases was determined to exceed the threshold.

23. The system of claim 22, wherein the computer is configured to continuously monitor the concentrations of the one or more gases received from the gas detection device to determine whether or not the concentration of the one of the monitored gases exceeds the threshold.

24. The system of claim 22, wherein the computer is configured to transmit the augmented image overlaid with the one or more numerical values of the concentration of the one of the monitored gases via a predetermined messaging technique to a predetermined party.

25. The system of claim 22,
wherein to become wirelessly connected to the gas detection device and the camera, the computer is configured to perform network discovery searching of a network to discover the gas detection device and the camera, the gas detection device and the camera being connected to the network, and
wherein after discovering the gas detection device and the camera, the computer is configured to logically associate the camera with the gas detection device such that when the computer determines that the concentration of the one of the monitored gases exceeds the threshold, the computer obtains the image from the camera.

26. The system of claim 25, wherein the gas detection device and the camera are wirelessly connected to the network.

27. The system of claim 22, wherein the computer is configured to perform object recognition on the augmented image to determine whether or not the concentration of the one of the monitored gases determined to exceed the threshold is caused by a triggering event which is not a cause for an alarm.

28. The system of claim 22, wherein the camera is integrated with the gas detection device.

\* \* \* \* \*